US007591797B2

(12) United States Patent
Hakonson et al.

(10) Patent No.: US 7,591,797 B2
(45) Date of Patent: Sep. 22, 2009

(54) FLUID OPERATED ACTUATORS AND PNEUMATIC UNLOADING ORTHOSES

(75) Inventors: Greg Hakonson, Dawson (CA); Christopher Denny, Victoria (CA); Scott Phillips, Victoria (CA); Mark Foster, Victoria (CA)

(73) Assignee: Pneu Medex Inc., Dawson City YT (CA)

( * ) Notice: Subject to any disclaimer, the term of this patent is extended or adjusted under 35 U.S.C. 154(b) by 259 days.

(21) Appl. No.: 10/564,971

(22) PCT Filed: Jul. 19, 2004

(86) PCT No.: PCT/CA2004/001040

§ 371 (c)(1),
(2), (4) Date: Jul. 24, 2006

(87) PCT Pub. No.: WO2005/007046

PCT Pub. Date: Jan. 27, 2005

(65) Prior Publication Data

US 2007/0197943 A1   Aug. 23, 2007

Related U.S. Application Data

(60) Provisional application No. 60/487,948, filed on Jul. 18, 2003.

(51) Int. Cl.
A61F 5/00 (2006.01)
A61H 1/00 (2006.01)
A61H 7/00 (2006.01)

(52) U.S. Cl. ............... 602/13; 602/1; 602/5; 602/20; 601/1; 601/84; 601/148; 601/151; 601/152; 128/DIG. 20

(58) Field of Classification Search ............ 602/13, 602/5, 1; 128/DIG. 20; 601/148–152, 1, 601/84
See application file for complete search history.

(56) References Cited

U.S. PATENT DOCUMENTS

| 1,589,670 | A | * | 6/1926 | Vartia ................... 602/36 |
| 3,521,623 | A | * | 7/1970 | Markley et. al. ........... 602/13 |
| RE34,883 | E | * | 3/1995 | Grim ..................... 602/13 |
| 5,450,858 | A | * | 9/1995 | Zablotsky et al. .......... 128/876 |
| 5,950,628 | A | * | 9/1999 | Dunfee ................... 128/874 |

(Continued)

FOREIGN PATENT DOCUMENTS

EP        0864308 A1    9/1998

(Continued)

OTHER PUBLICATIONS

International Search Report for PCT/CA2004/001040, International Searching Authority, Feb. 17, 2005, pp. 1-2.

*Primary Examiner*—Michael Phillips
*Assistant Examiner*—Tarla R Patel
(74) *Attorney, Agent, or Firm*—Oyen Wiggs Green & Mutala LLP

(57) ABSTRACT

A flexible fluid filled actuator has an elastic bladder and a guide surrounding the bladder. The guide has asymmetrical elastic properties. When the bladder is inflated the guide directs the bladder to expand preferentially in a selected direction or directions. The actuator has utility in the traction and/or unloading of portions of the body. A fluid-filled traction apparatus is disclosed which has particular advantages in spinal unloading.

27 Claims, 12 Drawing Sheets

U.S. PATENT DOCUMENTS

| | | | |
|---|---|---|---|
| 6,237,602 B1 * | 5/2001 | Nickels et al. | 128/874 |
| 2004/0010212 A1 * | 1/2004 | Kuiper et al. | 601/152 |
| 2004/0073150 A1 * | 4/2004 | Roballey | 602/36 |
| 2005/0143683 A1 * | 6/2005 | Waldridge et al. | 601/151 |

FOREIGN PATENT DOCUMENTS

| | | |
|---|---|---|
| GB | 1119904 | 7/1968 |

* cited by examiner

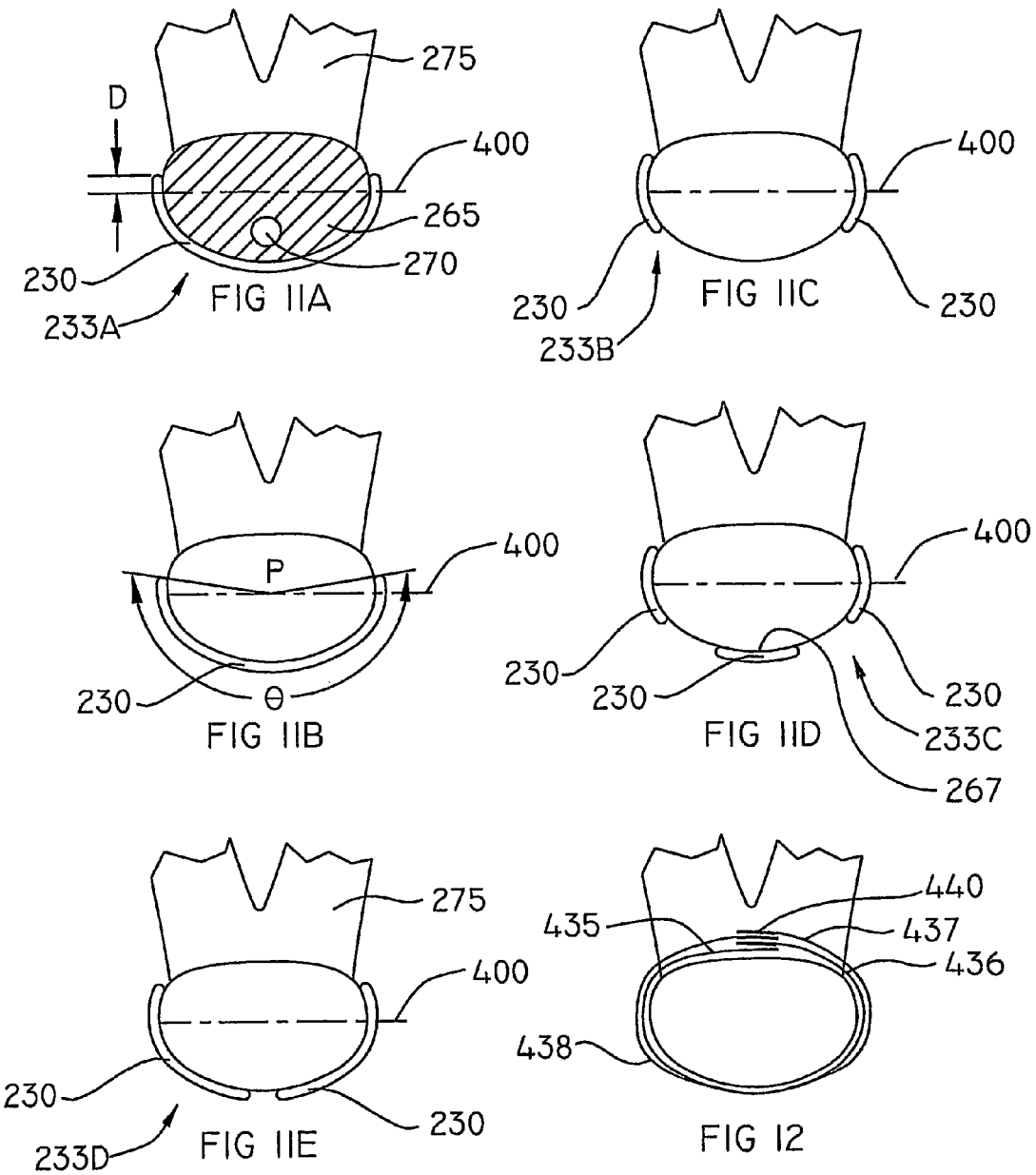

FLUID OPERATED ACTUATORS AND PNEUMATIC UNLOADING ORTHOSES

CROSS-REFERENCE TO RELATED APPLICATION

This application claims priority from and the benefit of U.S. application No. 60/487,948 filed on 18 Jul. 2003 which is hereby incorporated herein by reference.

TECHNICAL FIELD

The invention relates to actuators which may be used to apply forces to structures. The invention may be applied in a wide variety of fields. For example, the invention has application in orthoses and other medical devices for applying unloading forces to portions of the anatomy such as the lumbar spine, thoracic spine or cervical areas.

BACKGROUND

Back pain is a serious and potentially debilitating condition which affects a majority of people at some point in their lives. Back pain is currently the second leading cause of absenteeism from work after the common cold and accounts for 15% of sick leaves. In the United States alone back injuries are estimated to cause 100 million lost days of work annually. The lumbar region is the primary source of pain for 85% of back pain sufferers.

Many approaches are in current use to address lumbar pain including lumbar belts of various kinds, static traction devices, heat pads, physiotherapy, drugs, surgery, and exercise regimes.

Despite the fact that people have been developing devices to alleviate back pain for hundreds of years, there remains a need for effective apparatus for relieving back pain and for relieving other anatomical structures. Such apparatus should preferably be as comfortable to wear as practical and should interfere with a wearer's activities no more than necessary.

More generally, there is also a continuing need for actuators which overcome various disadvantages of currently available actuators in other fields. Actuators are used in a great many fields including industrial controls, automated equipment, undersea equipment, heavy lifting, medical catheters, etc. A wide range of actuators are available. Cylinders are the most common type for both pneumatic and hydraulic applications. Other actuator types include rolling diaphragms, and bellows. As previously stated, there are a wide variety of actuators which are available commercially.

It is desirable to provide actuators which are suitable for their intended applications and can be manufactured in a manner which is cost effective for the desired application.

SUMMARY OF THE INVENTION

This invention provides actuators which, upon inflation with a pressurized fluid, typically air, can apply force to an object. The actuators have a bladder guided by a flexible asymmetrically stretchable guide.

One aspect of the invention provides an actuator for applying a force to an object. The actuator comprises an inflatable bladder guided in expansion by a guide having asymmetrical expansion characteristics. The bladder has an inlet for inflating the bladder with fluid from a fluid source. In some embodiments the guide constrains the bladder to expand preferentially in one direction upon inflation. The guide may be integrated with the bladder in a unitary structure. In currently preferred embodiments the guide comprises a separate layer of material surrounding the bladder.

In some embodiments the guide comprises a layer of material penetrated by apertures. The apertures are arranged in an asymmetrical pattern so that the guide has a high-stretch direction and a low-stretch direction. In some embodiments the apertures comprise slits oriented parallel to the low stretch direction.

In some embodiments the guide comprises a layer of elastic material having a plurality of reinforcing members attached thereto. The reinforcing members extend in a low-stretch direction. The guide has an overall modulus of elasticity in the low-stretch direction substantially less than a modulus of elasticity in a high-stretch direction extending transversely to the reinforcing members.

The invention also provides apparatus for unloading a body part. The apparatus comprises first and second body-encircling members for attachment to a wearer's body on either side of the body part and an actuator according to the invention between the first and second body-encircling members. The body-encircling members may comprise, for example, belts which are the right length to attach around a wearer's hips and lower rib cage. In such apparatus the guide is oriented to control the expansion of the bladder to force the first and second body-encircling members apart upon inflation of the bladder.

Another aspect of the invention provides a fluid-operable actuator comprising four sheets of material. An innermost pair of the sheets is bonded together along one or more seams to form one or more fluid-tight bladders in fluid communication with a fluid source. An outermost pair of the sheets have asymmetrical stretch properties and are bonded along one or more seams to constrain the fluid tight bladder to expand preferentially in one direction upon inflation. In some embodiments one or both of the outermost pair of the sheets are weakened in a pattern of asymmetry features, which may comprise slits.

The invention also provides a method for applying force to an object. The method comprises coupling one end of an actuator according to an embodiment of the invention to the object, coupling another end of the actuator to another object, and inflating the actuator.

Further aspects of the invention and a features of embodiments of the invention are described below.

BRIEF DESCRIPTION OF THE DRAWINGS

In drawings which illustrate non-limiting embodiments of the invention,

FIG. 11A through 11E show sectional views through the torso of a subject wearing a traction device at the height of the upper pelvis: FIG. 11A shows a traction device on the back and sides; FIG. 11B shows how an actuator according to the invention may be disposed around a wearer's back and sides; FIG. 11C shows a traction device having two actuators located on the sides only; FIG. 11D shows an alternative embodiment having multiple actuators; and FIG. 11E shows an alternative embodiment having two actuators;

FIG. 12 shows a preferred embodiment of the encircling members;

DESCRIPTION

Figure 1:
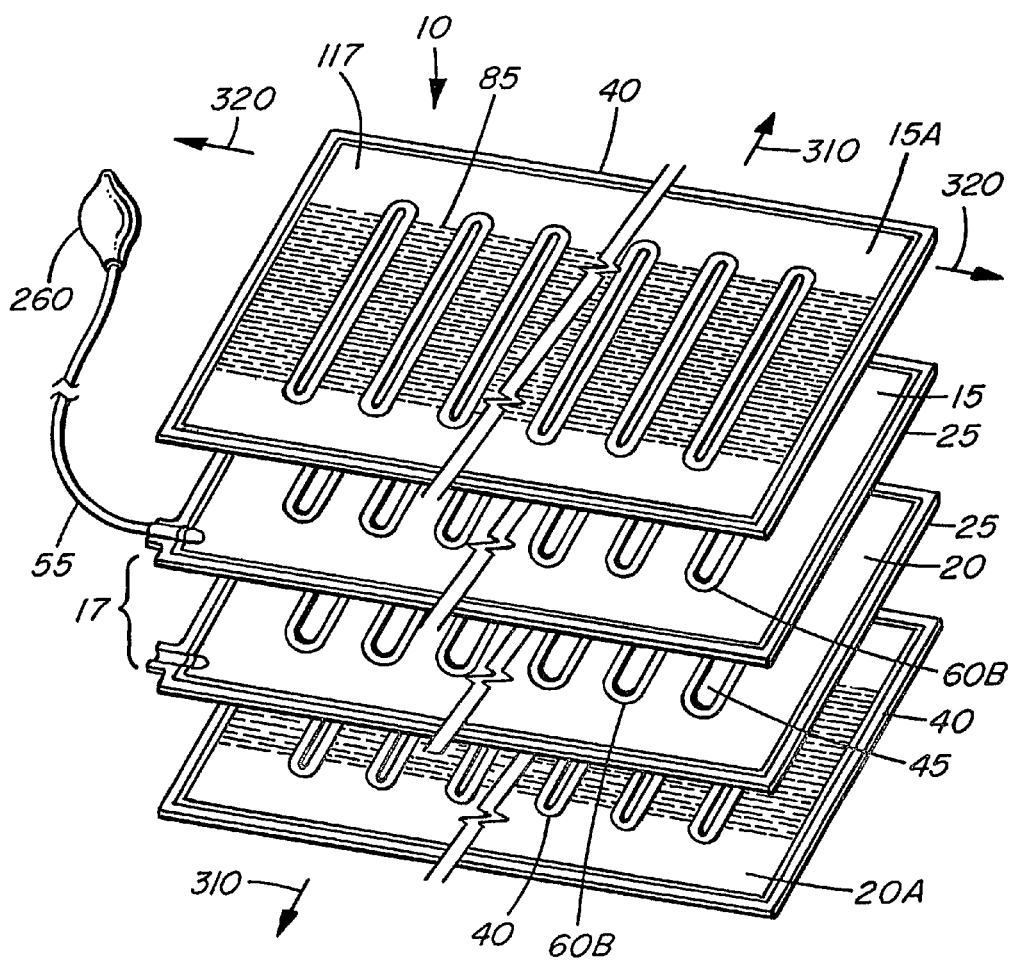
FIG. 1 shows an exploded schematic view of a planar actuator geometry according to the invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention provides actuators and force generators which comprise bladders that can be inflated with a pressurized fluid. The pressurized fluid is typically pressurized air or another pressurized gas. Pressurized liquids may be used to operate the actuators in some applications. Walls of the bladders have asymmetrical elastic properties. When the bladders are inflated they expand preferentially in selected directions. The bladder walls resist expansion in other directions.

Actuators according to the invention may be applied to forcing structures apart from one another. One area where actuators according to the invention have particular application is in devices for applying traction or "unloading" forces to parts of the human anatomy. For this reason, a number of traction (or "unloading") devices according to specific embodiments of the invention are described herein for purposes of illustrating the invention. The invention is not limited to such embodiments, however.

Apparatus according to the invention can take a wide range of forms. In some embodiments the asymmetrical expansion properties are provided by a guide comprising an outer layer of asymmetrically stretchable material which surrounds a bladder. The bladder is preferably elastic. The guide has a high-stretch direction and a stretch-resistant low-stretch direction. The guide stretches significantly more easily in the high-stretch direction than it does in the low-stretch direction. The high-stretch direction may vary from place-to-place over the guide. Preferably, the material of the guide is such that it remains elastically stretchable in its "high-stretch" direction even when it is substantially fully stretched in another direction.

The asymmetrical properties of the guide may be provided by any of a number of structures including one or both of:

The guide comprises a layer of material that is weakened with respect to stretching in one direction by selectively placed slits and/or apertures in the material. The material of portions of the guide away from the slits or apertures may be elastic or even substantially inelastic.

The guide may comprise oriented strengthening features which are formed in, attached to, and/or provided within the guide. The strengthening features cause the guide to resist stretching in one direction.

The guide may be made from a variety of materials with asymmetrical elastic properties. For example:

Suitable cloth materials may be used for the guide. For example biwoven materials are available having generally inelastic fibres running in one direction (a low-stretch direction) and elastic fibres running in a high-stretch direction which is typically at right angles to the low-stretch direction.

The guide may comprise a sheet of an elastic material such as urethane, silicone, neoprene, or other suitable elastomers which can be provided in sheet or tubular forms.

In some embodiments of such actuators both the bladder and the guide are made of the same material and manufactured by the same processes.

The guide may be extruded or moulded to have surface features having or inducing asymmetrical elastic properties.

The guide may comprise a layer of material having surface features made of the same or different materials affixed to it.

The guide may comprises fibres, strings and/or other oriented reinforcing bodies are attached to or moulded into the material of the guide.

It is not necessary that all parts of the guide have the same stretching properties. For example, in some embodiments, the material of the guide may have a lower elastic modulus on one side of an actuator than it does on an opposed side of the actuator. In such embodiments the actuator tends to bow when inflated. In some such cases the guide may be formed by affixing together two or more sections having dissimilar elastic properties.

The functions of the guide and bladder may be combined in a single layer of asymmetrically elastic material, which is also fluid impermeable, or may be provided in separate layers.

The guide may be provided in the form of a seamless tube. In the alternative, the guide may comprise one or more pieces of material joined together at seams. Where the guide comprises seams or connections between materials, any suitable methods may be used to provide the seams. For example, the seams may be made by sewing, heat sealing, adhesive bonding, or other suitable attachment method appropriate to the material of the guide. It is generally preferred that the guide seams are arranged so as to contain and constrain the bladder.

It is also possible that the guide is attached to the bladder or that seams in the bladder and guide are coincident at times.

A generally cylindrical actuator which expands preferentially in a longitudinal or axial direction can be provided by the invention. In such embodiments the bladder is inside the guide. The guide is tubular, when the bladder is inflated. The low-stretch direction is oriented circumferentially. As pressure within the bladder is increased, the guide limits expansion of the bladder in a radial direction. The guide allows the bladder to expand in an axial direction. Thus, as the bladder is inflated, the actuator becomes significantly longer in the axial direction but does not expand, at least not very much, in circumference.

An actuator may comprise several tubular portions which each operate in a manner similar to the cylindrical actuator described above. These tubular portions may be constructed separately or may be part of an integrated structure in which the guides, bladders, or both the guides and bladders of the different tubular portions are formed integrally with one another. In some embodiments of such actuators both the bladder and the guide are made of the same material and manufactured by the same processes. Examples of these constructions are described below.

In some embodiments the actuator has a flat configuration and the guide comprises two layers of asymmetrically elastic material which are suitably joined together, for example, by welding, sewing, suitable adhesive processes, or otherwise. The guide is disposed to substantially constrain the expansion of the bladder in the low-stretch direction and to channel the expansion of the bladder in one or more high-stretch directions as the bladder is inflated. In some such embodiments, expansion of the bladder is channelled to be greatest in a direction lying substantially in a plane of the actuator.

In some embodiments, the bladder comprises two layers of elastic material which are joined by welding or adhesives or other suitable means to form a generally planar structure having internal passages for receiving a fluid. Some or all of the passages may be interconnected with one another so that they may be pressurized from a single source of pressurized fluid. The interconnections may take the form of manifolds running along two opposite edges of the bladder for example feeding a series of generally parallel passages. The guide may be configured so that the passages become elongated as the bladder is inflated, thereby forcing the manifolds apart from one another. Such a configuration can provide convenient stiffness and mountability in addition to providing expansion. The passages may all expand at substantially the same rate so that the relative orientation of the manifolds is preserved during expansion (for example, the manifolds may remain parallel with one another).

In the alternative, the passages may be arranged so that they expand at different rates with the result that the relative orientation of the manifolds changes as the actuator is inflated (for example, one manifold may become progressively more tilted relative to the other manifold as the actuator is inflated) or that the shape of one manifold may be changed (for example, one of the manifolds may become progressively more curved as the actuator is inflated).

Another form of actuator which provides interconnections between fluid passages is configured like a quilt with interspersed islands of contact between the two sides of the bladder and guide structures.

Referring now to the accompanying figures, FIG. 1 shows a layered generally flat actuator 10. The plane of actuator 10 may curve gently to fit around a body part for example but in the uninflated state, actuator 10 is locally generally flat. Actuator 10 has a bladder 17 which is defined between upper bladder sheet 15 and lower bladder sheet 20. Bladder sheets 15 and 20 are each composed of an elastic material. Bladder sheets 15 and 20 are joined by one or more seams 25 to define at least one sealed fluid chamber.

The material of sheets 15 and 20 may, for example, be polyurethane. Urethane makes a very good bladder material because it has suitable elastic properties and is reasonably easy to work with. Urethane is commonly welded using processes such as radiofrequency (RF) welding. RF welding is inexpensive and reliable. A suitable bladder 17 can be made for example by welding two sheets of urethane together along one or more seams.

Bladder 17 is in fluid communication via fluid connection 55 with a pressurized fluid source 260 which is illustrated as a squeeze bulb but could also be a different type of manual pump or a compressed gas vessel or an electric pump for example. Fluid source 260 could supply any suitable compressed fluid such as air or another gas or water or oil or another liquid. Fluid source 260 could also supply expanding foam to bladder 17 in the case where a permanently expanded actuator was desired. Bladder 17 can be inflated by permitting fluid to flow from fluid source 260 into bladder 17.

Figure 5A:
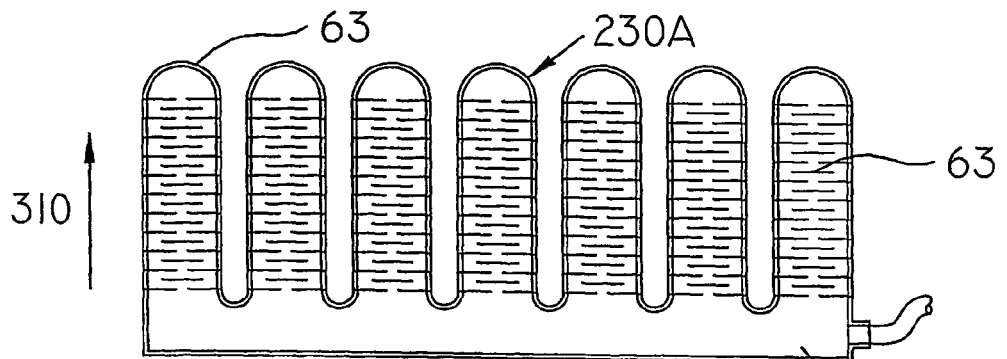
FIG. 5A shows a planar actuator having finger-like projections.

To keep actuator 10 from expanding too much out of its plane, internal seams 60B are provided. Seams 60B may form the boundaries of islands as shown in FIG. 1 or may run to edges of bladder 17 as shown in FIG. 5A. The islands are sealed from the fluid passages defined in the bladder. In the embodiment shown in FIG. 1 bladder 17 has apertures 45 within the islands formed by internal seams 60B.

The thickness of actuator 10, when inflated, is determined, in part, by the spacing of seams 60B in a transverse direction extending generally perpendicular to the tubular passages defined within bladder 17 between adjacent seams 60B. Making seams 60B closer together results in smaller passages and a thinner actuator 10. Making seams 60B farther apart results in larger passages which permits actuator 10 to be thicker when fully inflated. For example, a prototype lumbar unloading device having seams 60B separated by roughly 1½ inches has been found to provide a satisfactory balance between maximum inflated thickness and stiffness when inflated.

Bladder 17 is located within a guide 117 (FIGS. 1 and 2) which directs the expansion of bladder 17 when it is inflated. Guide 117 has a low-stretch direction 320 and a high-stretch direction 310. The elastic modulus of guide 117 is higher in direction 320 than it is in direction 310 (i.e. it takes a greater force to stretch the material of guide 117 by a given amount in direction 320 than in direction 310).

Figure 2:
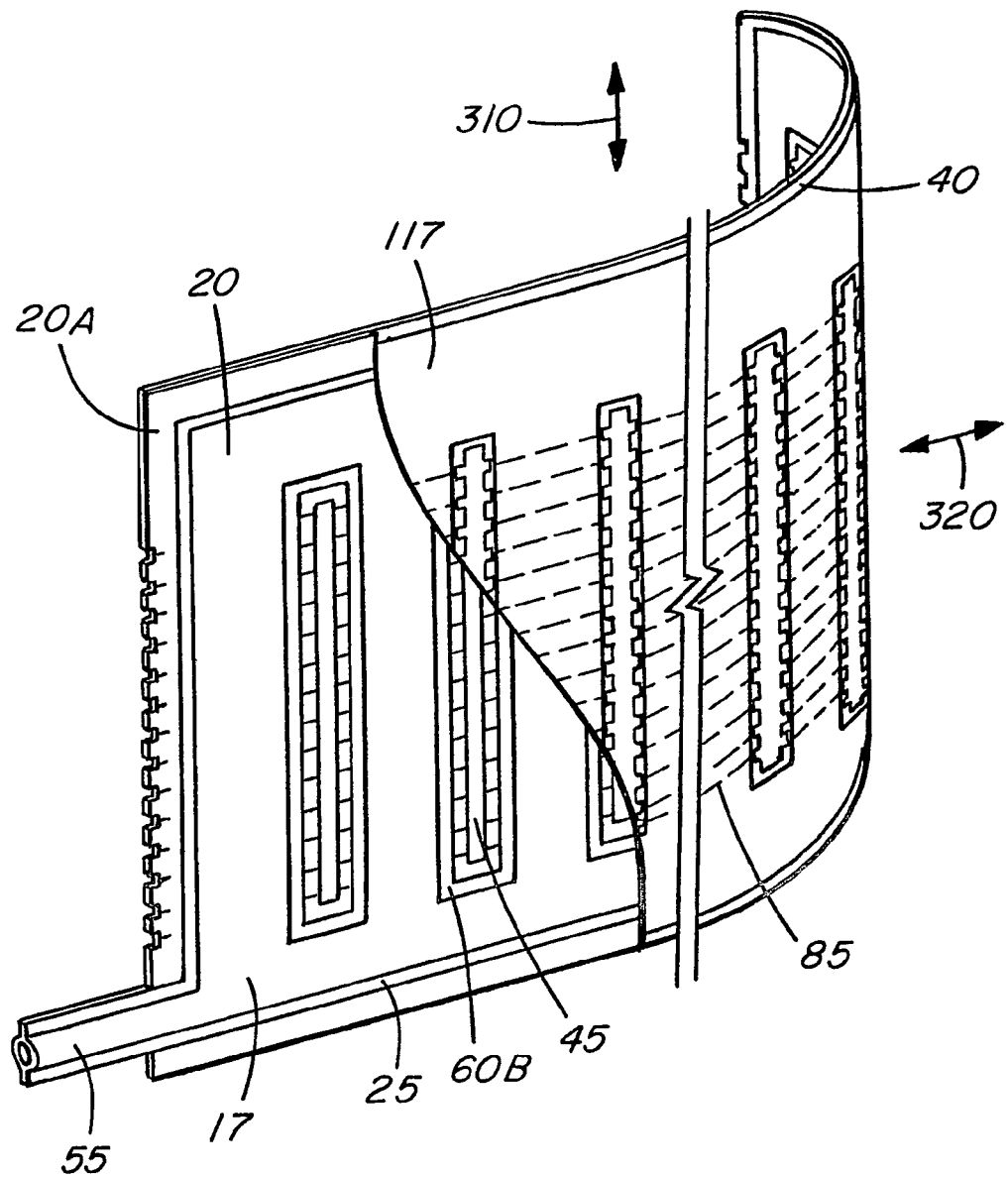
FIG. 2 shows a cutaway view of the actuator shown in FIG. 1.

The asymmetrical elastic properties of guide 117 may be provided in any suitable manner. In the illustrated embodiment, guide 117 is formed by two guide sheets 15A and 20A. In the embodiment of FIGS. 1 and 2, sheets 15A and 20A are made from a layer of material which has elastic properties which have been made asymmetrical, or more asymmetrical, by the provision of asymmetrical features 85. In the illustrated embodiment, features 85 comprise slits. The slits extend parallel to low-stretch direction 320 and are transverse to preferred stretch direction 310.

In alternative embodiments, features 85 could comprise other apertures, molded features, or weakened areas. In other alternative embodiments, sheets 15A and 20A are made from cloth with asymmetrical elastic properties. For example, sheets 15A and 20A may be made from an asymmetrically elastic knitted cloth. Some suitable cloths are bi-woven.

If guide 117 and bladder 17 are made from the same material then the material of guide 117 is preferably significantly thicker, for example at least twice as thick, as the material of bladder 17 so that it has a significantly greater modulus of elasticity than the material of bladder 17 in its low-stretch direction 320. In the case of polyurethane a thickness in the range of 0.001 inch to 0.005 inch has been found to work quite well for bladders 17 used for spinal traction and designed for inflation with air at a pressure of roughly 10 psig. With such bladders a guide 117 made from polyurethane sheets having thicknesses in the range of 0.005 inch to 0.050 inch may be used. These thicknesses are by way of example only.

Guide sheets 15A, 20A are joined together along seams 40 which may be continuous or intermittent and which may be sewn or welded or joined with adhesive or other suitable method. Guide seams 40 are arranged so that guide 117 surrounds bladder 17. Guide seams 40 may overlay bladder seams 25 but preferably do not. In some embodiments of the invention, guide seams 40 running in a direction parallel or substantially parallel to high-stretch direction 310 are intermittent so that the guide seams do not restrict expansion of the guide in high-stretch direction 310.

Where bladder 17 is penetrated by apertures 45, apertures 45 may provide access for guide seams 40 to be welded or otherwise provided.

FIGS. 3A to 3K illustrate various asymmetry features 85 that may be provided on guide 117 to cause guide 117 to have asymmetrical elastic properties. These figures illustrate various possible combinations of slits 105 and cutouts 100 which can be applied to one or both of sheets 15A or 20A to selectively weaken the sheets in the high-stretch direction so as to cause the elastic properties to become asymmetrical. Providing slits 105 has the advantage over providing cutouts 100 that the operation of cutting slits 105 does not produce any cut out waste parts. Slits 105 do not need to be straight lines, as shown, but could have other shapes.

Features 85 may be made, for example, by laser cutting or die cutting. As shown in some of the illustrated embodiments, asymmetry features 85 may extend to the edges of the guide 117 and through guide seams 40 to facilitate stretching of guide seams 40.

Where asymmetry features 85 weaken the material of guide 117 they are preferably laid out in a manner that provides lateral bands 90 (FIG. 3A) in which the material of sheet 15A is substantially unbroken. Lateral bands 90 serve to minimize the stretch in low-stretch direction 320. Features 85 may also be laid out to form axial bands 95 extending generally parallel to high-stretch direction 310.

Figure 3A:
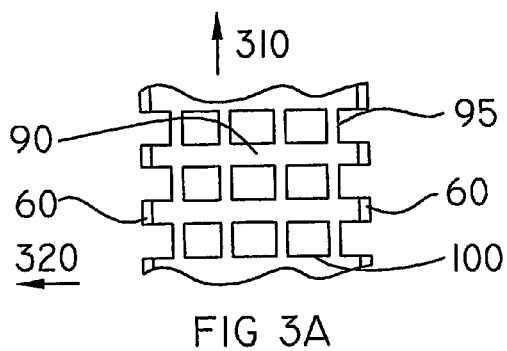
FIGS. 3A to 3G show guides which are selectively weakened according to various embodiments of the invention.
Figure 3F:
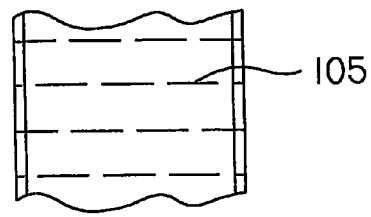
Figure 3B:
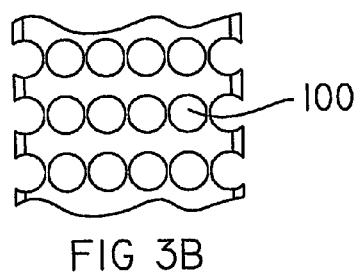
Figure 3G:
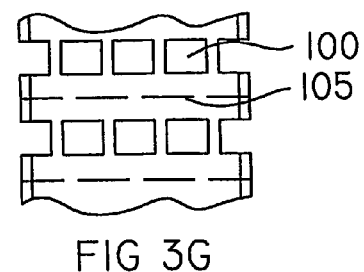
Figure 3C:
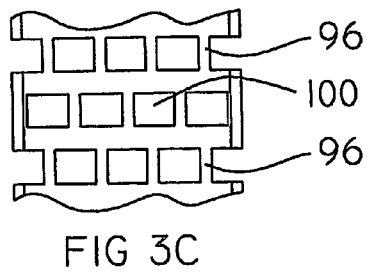

As shown in FIG. 3C, the modulus of elasticity in high-stretch direction 310 can be reduced by offsetting features 85 so that there is no continuous band of material in the material of sheet 15A which runs in high-stretch direction 310. In the embodiment of FIG. 3C, upon inflation of bladder 17, guide 117 expands preferentially in direction 310 by a combination of stretch of axial band portions 96 and distortion of cutouts 100 or slits 105 (not shown in FIG. 3C).

The patterns of asymmetry features 85 are not required to be continuous. Guide 117 may be patterned with features 85 only in selected regions in which guide 117 should permit bladder 17 to expand. The pattern of features 85 may chosen so that the high-stretch direction varies from place to place or so that the elastic modulus varies from place to place.

Figure 3H:
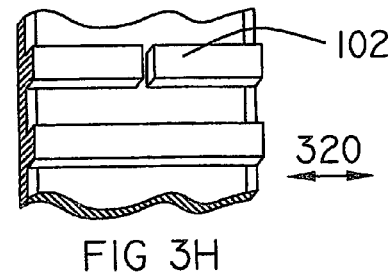
FIGS. 3H and 3J to 3K show guides which have had features added to them to introduce asymmetrical elastic properties according to various embodiments of the invention.
Figure 3D:
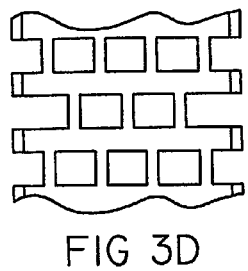
Figure 3J:
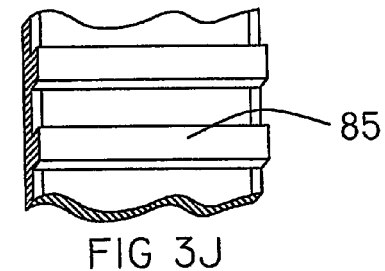
Figure 3E:
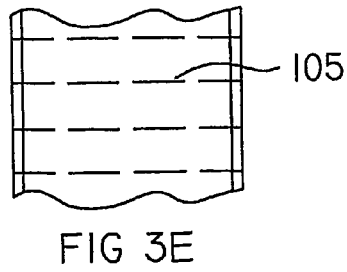
Figure 3K:
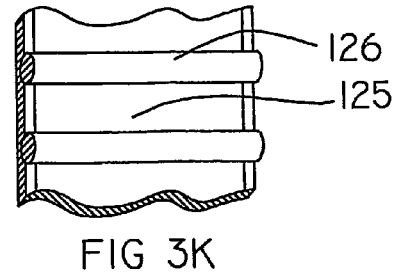

Asymmetry features 85 may in addition or alternatively be of a type which reinforces or strengthens portions of the material of guide 117. For example, FIG. 3H shows surface elements 102 bonded onto the guide material in order to selectively increase the stiffness in the low-stretch direction 320. FIG. 3J shows a similar arrangement in which features 85 are molded or extruded in place. FIG. 3K shows an embodiment in which long thin features 126, such as lengths of fibre or yarn, are bonded to the surface of guide material 125 or embedded in guide material 125. Features 126 may each extend around the circumference of a tubular actuator portion or may each extend only partway around a tubular actuator portion.

Figure 4A:
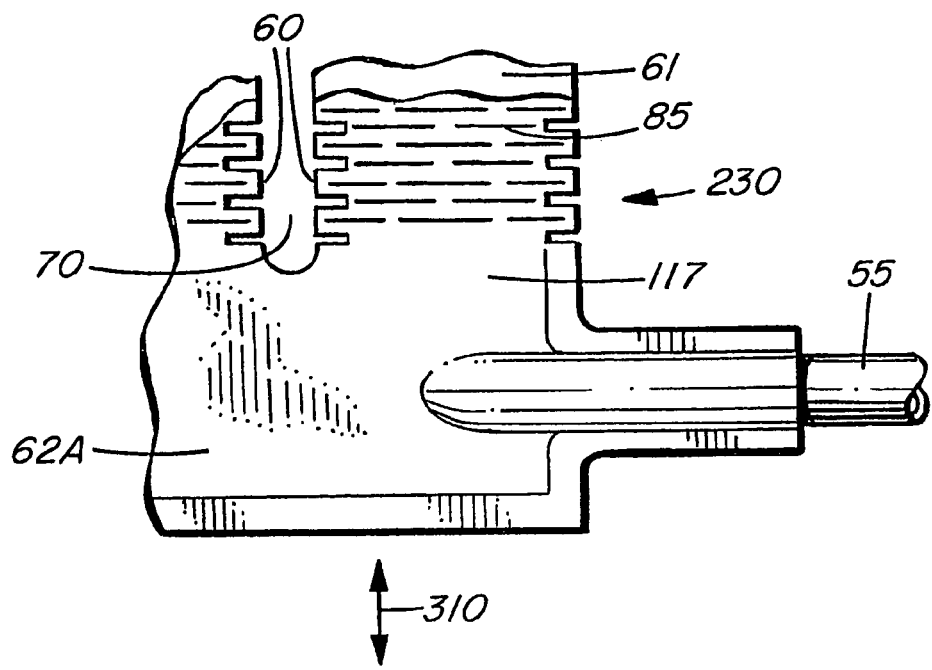
FIG. 4A is a cutaway view of a portion of an actuator according to the invention, in an uninflated condition.
Figure 4B:
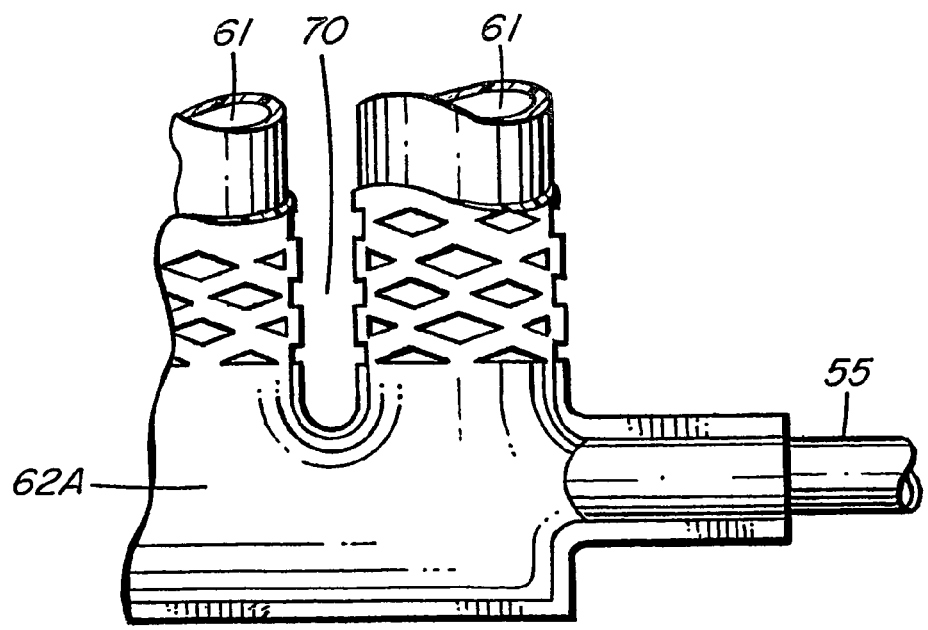
FIG. 4B is a view of the actuator of FIG. 4A in an inflated condition.

FIG. 4A shows a portion of an actuator 230 according to the invention. In actuator 230, seams 60 are arranged to provide a number of parallel passages 61 which extend parallel to high-stretch direction 310. Upon inflation with pressurized fluid delivered through connection 55, passages 61 blow up so that they assume a shape in cross section that is generally round, as shown in FIG. 4B. Upon inflation, actuator 230 assumes a configuration in which passages 61 provide a series of parallel columns which are joined at one end by transverse manifold 62A. At the other end the columns may be joined by another manifold (not shown). The adjacent passages 61 tend to reinforce one another against bending or buckling in the plane of actuator 230, especially where passages 61 are closely spaced. In the illustrated embodiment, asymmetry features 85 are provided in the portions of guide 117 corresponding to passages 61 but not in the portions of guide 117 corresponding to manifolds 62A.

Guide 117 permits passages 61 to stretch longitudinally, or generally axially, as they are inflated, thereby forcing manifold 62A and the remote ends of passages 61 apart. Actuator 230 may be made to have passages 61 of any reasonable lengths.

As shown in FIG. 4B, apertures 70 in guide 117 may be provided between adjacent passages 61. Apertures 70 permit passages 61 to separate from one another as actuator 230 is inflated, thereby preventing adjacent passages 61 from pulling on one another and distorting actuator 230.

FIGS. 5A through 5H show actuators according to a number of different embodiments of the invention. The locations and types of asymmetry features are not shown in detail in these Figures. The actuator 230A of FIG. 5A has a simple geometry providing a manifold 62 and a plurality of parallel fingers 63 extending from manifold 62. Upon inflation, fingers 63 become elongated. Actuator 230A could be used, for example, to force two members apart by providing a pocket attached to one of the members to receive manifold 62 and one or more pockets on the other member to receive fingers 63.

Figure 5B:
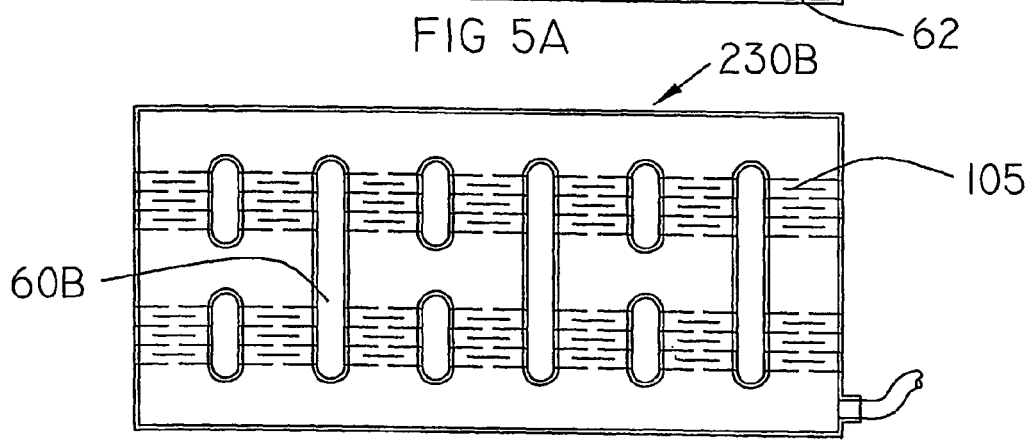
FIGS. 5B, 5C, 5D show planar actuators with various seam configurations and various arrangements of asymmetrical features.
Figure 5C:
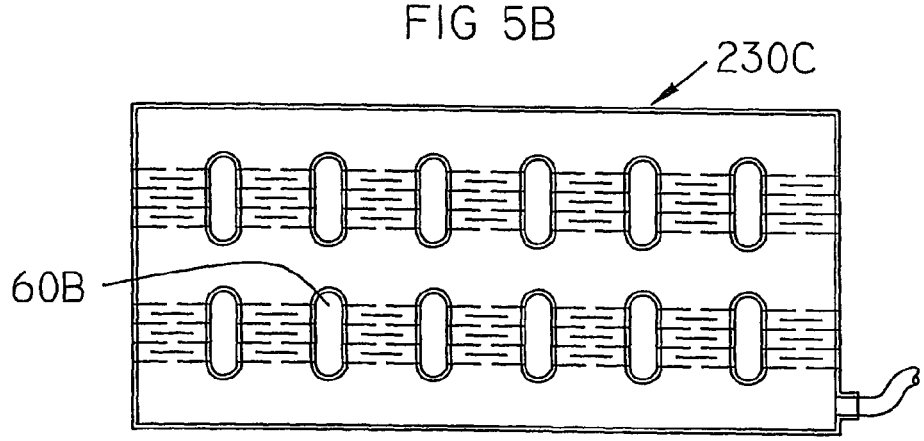
Figure 5D:
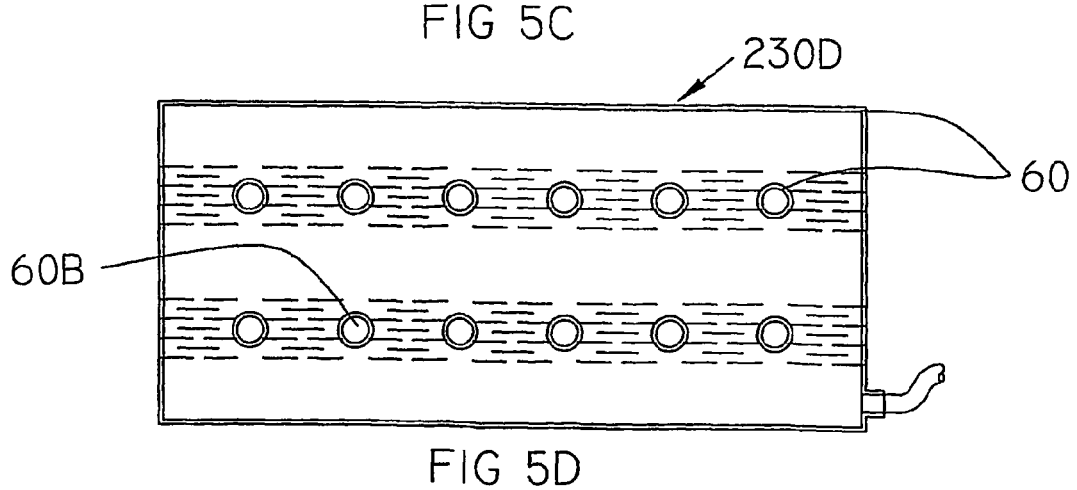

FIGS. 5B, 5C and 5D respectively show actuators 230B, 230C and 230D which have rectangular planar configurations and various configurations of inner seams 60B.

Figure 5H:
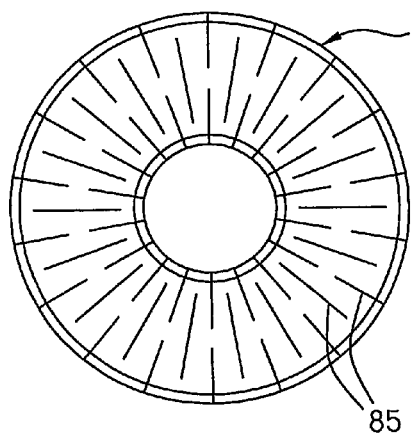
FIG. 5H shows an actuator according to another toroidal embodiment in which asymmetry features are arranged to promote an increase in the diameter of the toroid with a less significant increase in the thickness.
Figure 5F:
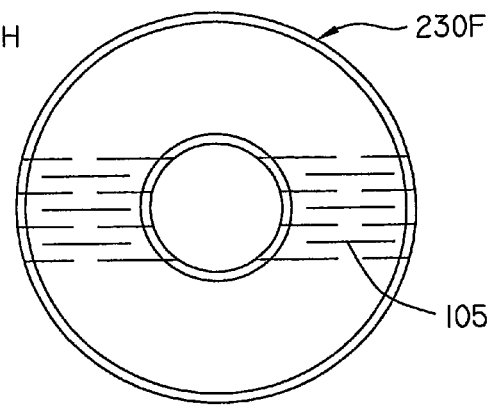
FIG. 5F shows an actuator having a toroidal configuration and expands elliptically when inflated.

FIG. 5F shows an actuator 230F which has a toroidal bladder. Actuator 230F has selectively located guide slits 105 configured to enable elliptical expansion of the actuator. As actuator 230F is inflated it adopts an oval configuration. The oval configuration becomes more elongated as actuator 230F is inflated more.

Figure 5G:
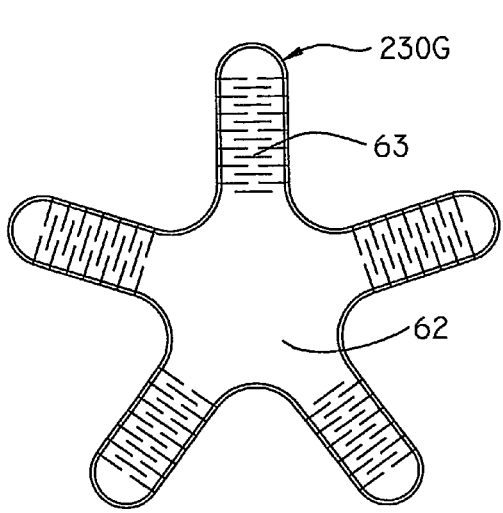
FIG. 5G shows an actuator having arms extending in a radial configuration.
Figures 5J, 5K:
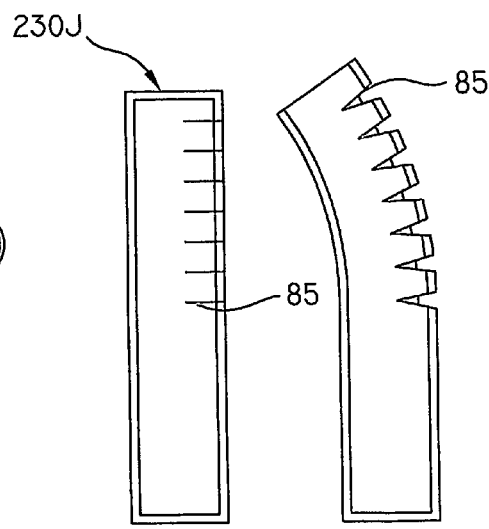
FIGS. 5J and 5K are plan views of an actuator respectively in uninflated and inflated states.

FIG. 5G shows an actuator 230G according to an embodiment with fingers 63 oriented outward in a radial pattern from a central manifold 62. Each of fingers 63 extends radially outwardly from manifold 62 as actuator 230G is inflated. FIG. 5H shows an actuator 230H according to another toroidal embodiment in which asymmetry features 85 are arranged to promote an increase in the diameter of the toroid with a less significant increase in the thickness. FIG. 5J shows an uninflated tubular actuator 230J having asymmetry features 85 concentrated along one of its sides. FIG. 5K shows actuator 230J after inflation. In its inflated state, actuator 230J is bent.

Figure 6:
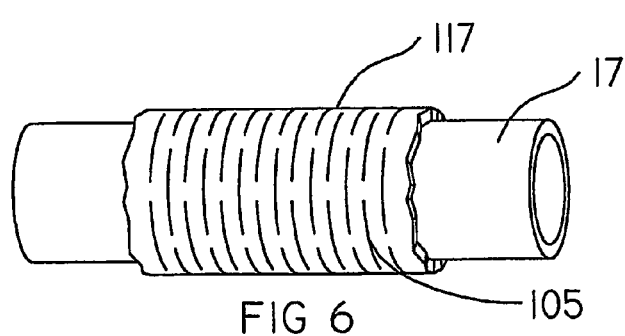
FIG. 6 shows a tubular actuator having an inflatable bladder inside a tubular guide, in an uninflated condition.
Figure 7:
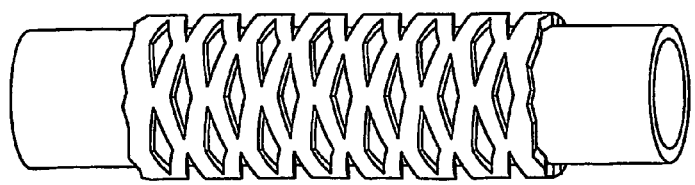
FIG. 7 shows the actuator of FIG. 6, in an inflated condition.

FIGS. 6 and 7 shows a portion of a tubular bladder 17 within a tubular guide 117. Slits 105 (FIG. 6) are oriented in a circumferential direction on guide 117. In this configuration either or both of bladder 17 and guide 117 may be formed from an elastic tube. The tube(s) may be made from any suitable materials including materials such as silicone. When bladder 17 is inflated, guide 117 constrains the expansion of bladder 17 so that it expands primarily axially, as shown in FIG. 7.

General Applications

Actuators according to the invention may be used to apply forces between two objects or two parts of the same object. In such embodiments, an actuator is coupled between a pair of connecting means. The connecting means attach to the object or objects. When the actuator is inflated it expands preferentially in a direction which forces the connection means to apply force to the object or objects in a desired direction.

The actuator may attach to the connecting means in any of various ways. In some embodiments, an end of the actuator is received in a sleeve or pocket on the connecting means. In other embodiments, an end of the actuator bears against a bearing surface of the connecting means. The actuator may be attached to the connecting means using a suitable attachment means such as stitching, a suitable adhesive, hook and loop fasteners, welding, fasteners such as bolts or hooks passing through apertures provided on the actuator, or the like.

The connecting means may each comprise one or more members, which may be flexible or rigid, and which have a mechanism for delivering force to a desired location on an object. By way of example, the connecting means may comprise object attachment means for delivering force to an object such as a belt which wraps around a portion of the object, a member which can be affixed to the object using suitable fasteners such as bolts, screws, adhesives, hooks, rivets or the like, an abutment surface which can be brought to bear against a corresponding surface on the object, or the like.

Figure 8:
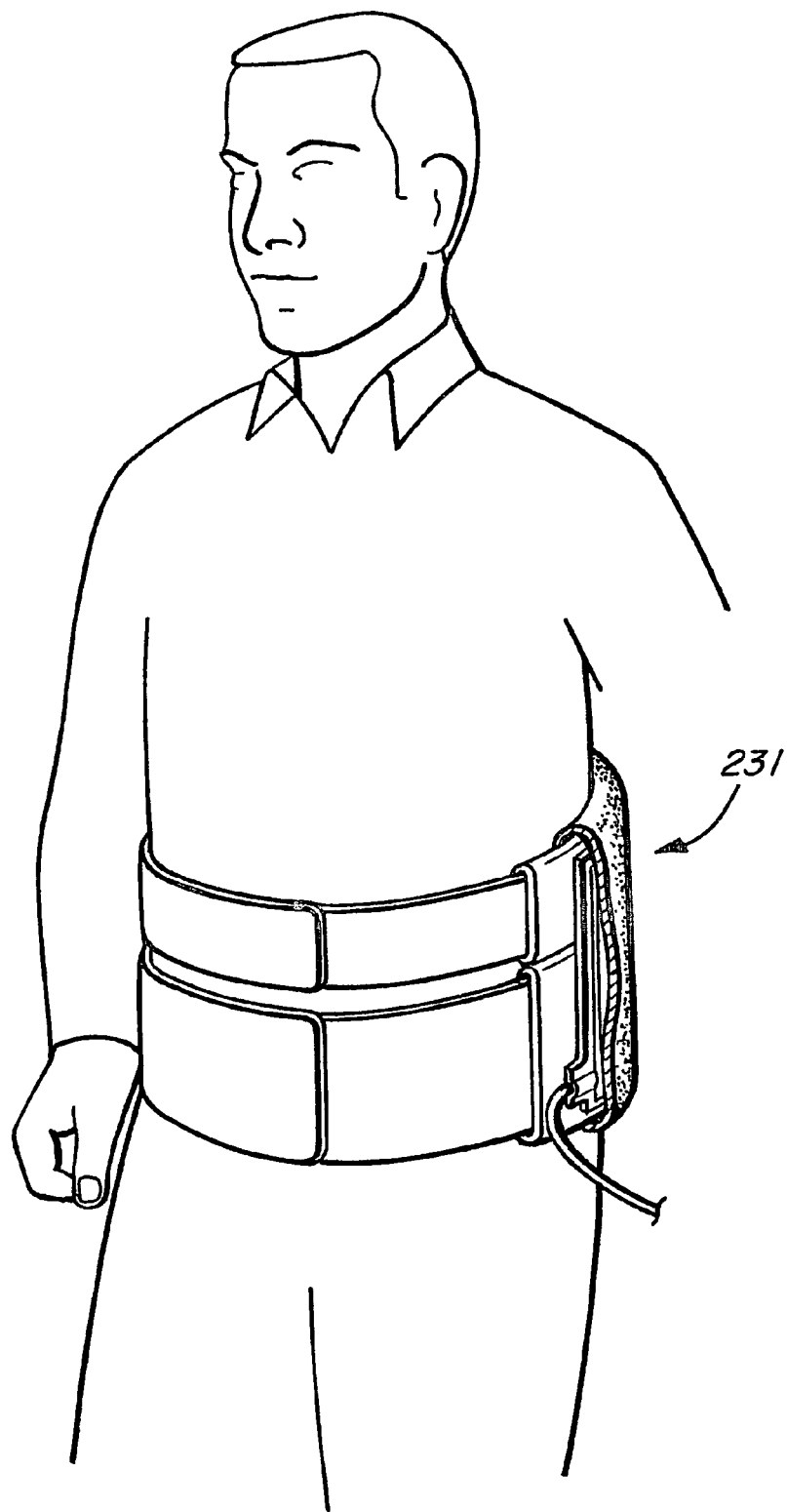
FIGS. 8 and 9 are perspective news of a wearer wearing apparatus according to the invention for unloading the wearer's lumbar spine.
Figure 9:
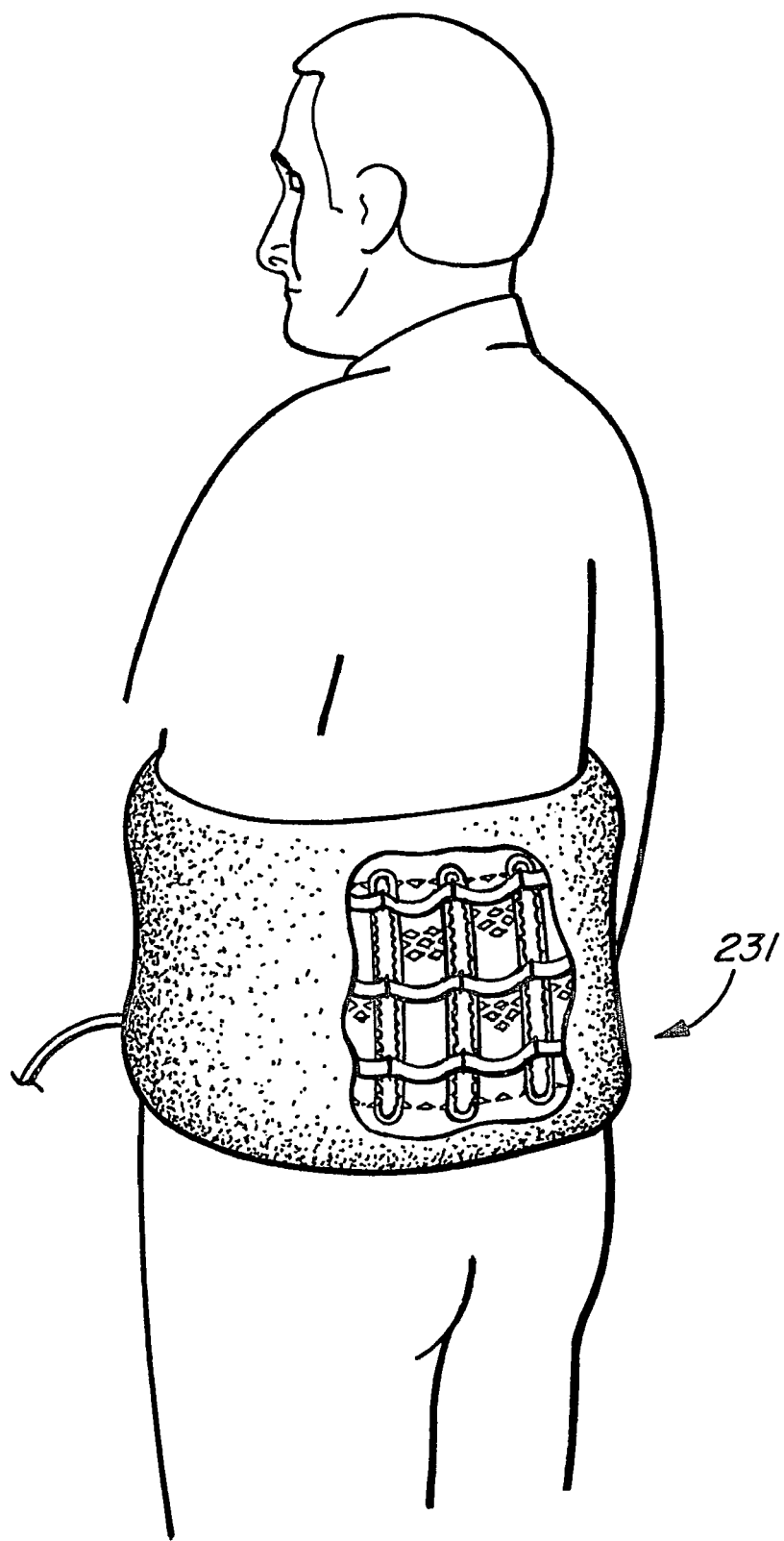
Figure 10:
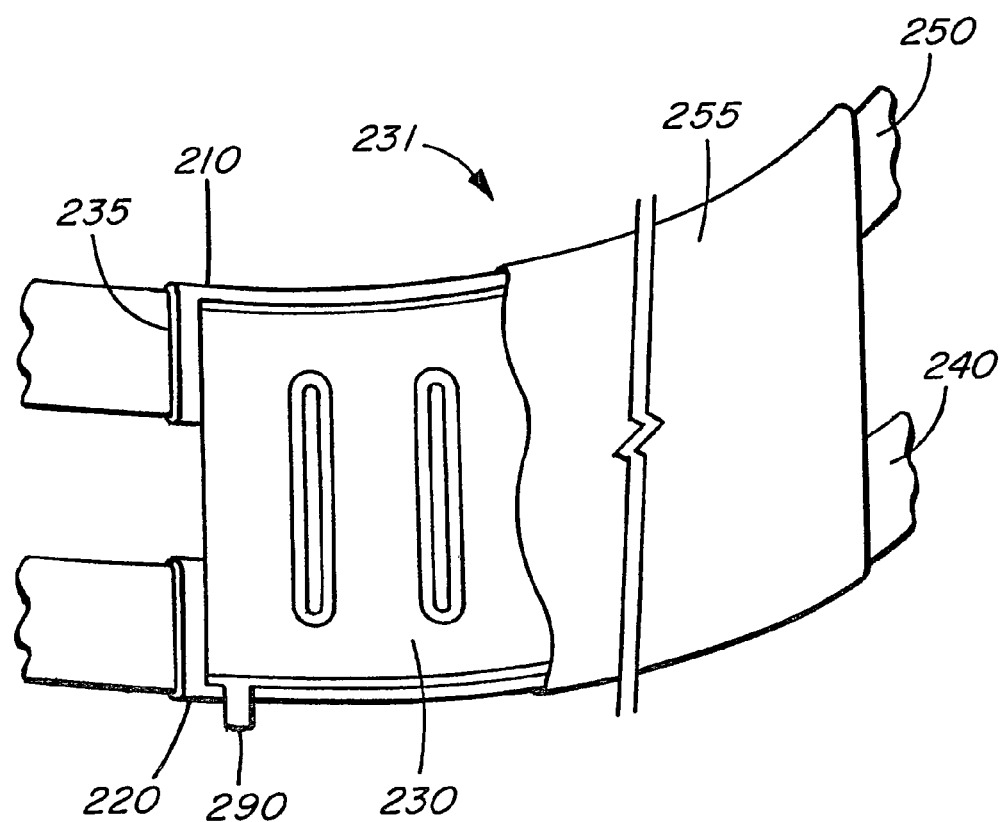
FIG. 10 shows the application of a flat actuator to a traction device.

Embodiments for Supporting and/or Applying Traction or Unloading Forces to Anatomical Structures FIGS. 8 and 9 show a person wearing apparatus 231 for unloading the wearer's lumbar spine. FIG. 10 shows apparatus 231 in more detail. As shown in FIG. 10, apparatus 231 includes an extending actuator 230. Apparatus 231 has two body-encircling members, an upper belt 250 and a lower belt 240. An upper sleeve 210 is attached to or otherwise accommodates upper belt 250 and a lower sleeve 220 is attached to lower belt 240. Sleeves 210 and 220 respectively receive upper and lower edges of actuator 230 and transfer extension forces from actuator 230 to encircling members 240 and 250, tending to force them apart. In a currently preferred embodiment, sleeves 210 and 220 are made from polyurethane and are welded directly to actuator 230 which is also made from polyurethane.

It can be seen from FIGS. 8, 9 and 10 that unloading devices for supporting a wearer's lumbar spine can be provided which permit a wearer to sit down comfortably even when the device is being used. It has been found that acceptable back support can be obtained by providing one or more thin flat actuators which extend around a wearer's back and sides. A properly designed support can develop substantial unloading forces without tending to tip the torso forward significantly. The lack of an actuator in the wearer's front (adjacent to the wearer's abdominal muscles) allows a wearer to sit comfortably for long periods while wearing the support.

Some embodiments include stiffeners 235 (FIG. 10) which may be affixed to encircling members 250 and 240, for example by sewing, welding or with suitable adhesives. Stiffeners 235 reinforce the encircling members so that they can take loads without curling over. Cover 255 which is ideally made from a stretchable and soft material may cover actuator 230 and at least a portion of belts 240 and 250 to provide enhanced protection, washability and wearer comfort.

Actuator 230 is in fluid communication with pressurized fluid source 260 (not shown in FIG. 10). A pressure relief vent 290 is provided to prevent overinflation of actuator 230 both to prevent damage to actuator 230 and to prevent excessive unloading force from being applied to a wearer. The pressure at which pressure relief vent 290 opens may be customized to suit the needs of the wearer. A manual pressure release (not shown) may also be provided to permit the wearer to release fluid from actuator 230 to reduce the unloading force while wearing or prior to removal of the unloading apparatus. Some embodiments may allow fluid to be released from actuator 230 through fluid connection 55.

FIG. 11A shows a lumbar spine unloading device 233A in which a single actuator 230 having a number of interconnected air passages is used for applying traction on the back and the sides of a wearer's torso 275. This design minimizes the number of fluid connections and applies a well balanced force. Dimension D indicates the forwardmost actuator position relative to torso coronal midline 400. In practice D should typically not exceed about 5" in order that no pneumatic components interfere with the wearer's thighs when sitting down. The distance D to which actuator 230 can project past coronal midline 400 depends to some degree on the size of the person wearing device 229.

The air passages of actuator 230 may extend parallel to one another. When inflated the passages may form a continuous palisade-like arrangement of closely-spaced passages (as shown for example in FIGS. 8 and 9) between the foremost actuator position on one side of the wearer's body, around the wearer's back to the foremost actuator position on the other side of the wearer's body. Each of the passages may be separated from the adjoining passage or passages by apertures, material that has a low modulus of elasticity or material that is initially slack. This permits the walls of the adjacent passages to pull slightly apart from one another without distorting the overall configuration of the actuator as the passages are inflated. In preferred embodiments, when the passages are inflated, the walls of adjacent passages are spaced apart from one another by distances that are smaller than the widths of the passages in the plane of actuator 230.

FIG. 11B illustrates that in preferred embodiments of the invention the actuator extends through an angle θ which is less than 270 degrees as measured relative to a central point P on the wearer's torso coronal midline 400. This provides a device which is substantially open in the front of the wearer to provide leg clearance when the wearer is sitting.

FIG. 11C shows a spine unloading device 233B having two individually adjustable actuators. Each of the actuators is located adjacent one of a wearer's hips. Torso midline 400 passes through both actuators. In the configuration of FIG. 11C it would be possible to apply more force on one side of the wearer than the other. This may be desirable for example, if the wearer has a condition such as scoliosis.

FIG. 11D shows a spine unloading device 233C having a configuration with two actuators 230 on the hips and another on the back 267 of the wearer's torso 275. FIG. 11E shows a spine unloading device 233D having a configuration with two actuators 230, each of which wraps around from the wearer's back to the wearer's hips.

As described above with reference to the actuator of FIG. 11A, the actuators 230 of the embodiments shown in FIGS. 11C, 11D and 11E may have closely-spaced air passages arranged to provide a palisade-like arrangement of generally parallel air passages when inflated.

FIG. 12 shows a possible construction for an encircling member. Inner straps 435 and 436 are of high stiffness. In one embodiment inner straps 435 and 436 are made from a low elasticity material such as nylon webbing. Optionally some elasticity may be added or a more elastic material used to achieve some stretchiness. Strap ends 440 may have hook and loop fastening material mounted to them to facilitate attachment of the strap ends 440 to one another. Outer straps 437 and 438 are preferably much more elastic than inner straps 435 and 436. These are tensioned sequentially and attached such that the first outer strap 437 is attached to second inner strap 436 and the second outer strap 438 is attached to the first outer strap 437. In this way a good attachment to the body can be achieved in a sequential way without significant application of force at any individual stage.

Figure 13A:
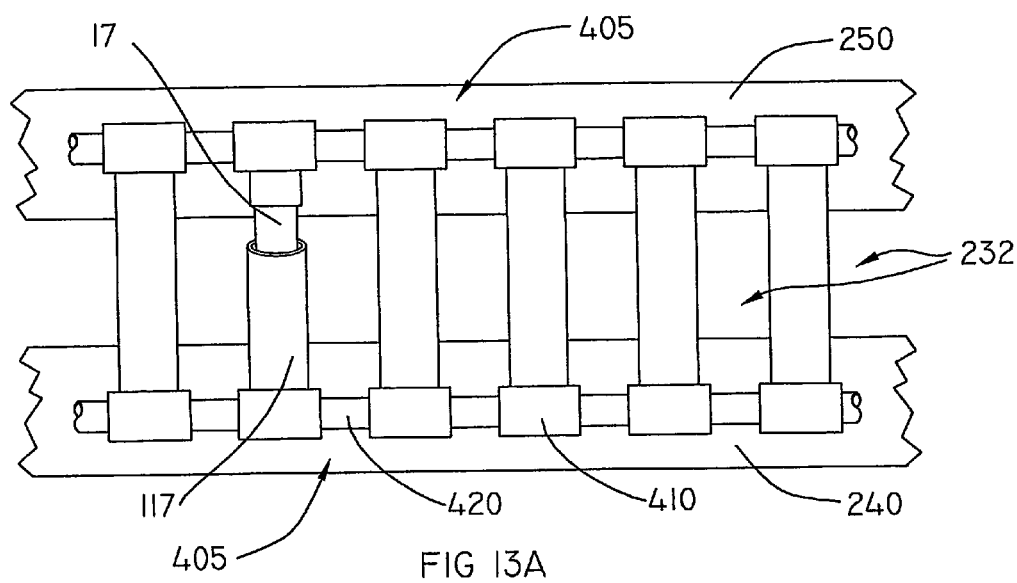
FIG. 13A is a cut away view of a traction device having tubular actuators connected by manifolds.

FIG. 13A shows a human traction device in which the actuator comprises a number of tubular actuators 232 which extend between manifolds 405. Manifolds 405 comprise T-fittings 410 and manifold tubing 420. Bladders 17 are made from tubular elastic material such as sections of silicone tubing and are joined at their ends to T-fittings 410. Guides 117 are tubes of material with asymmetrical elastic properties arranged to facilitate lengthening of the tubes in response to the introduction of pressurized fluid with a limited radial expansion. Guide tubes 117 may be cut from tubular material or assembled from flat material which has been joined at one or more seams. The actuator is joined to lower belt 240 and upper belt 250 in order to provide a separating force.

Figure 13B:
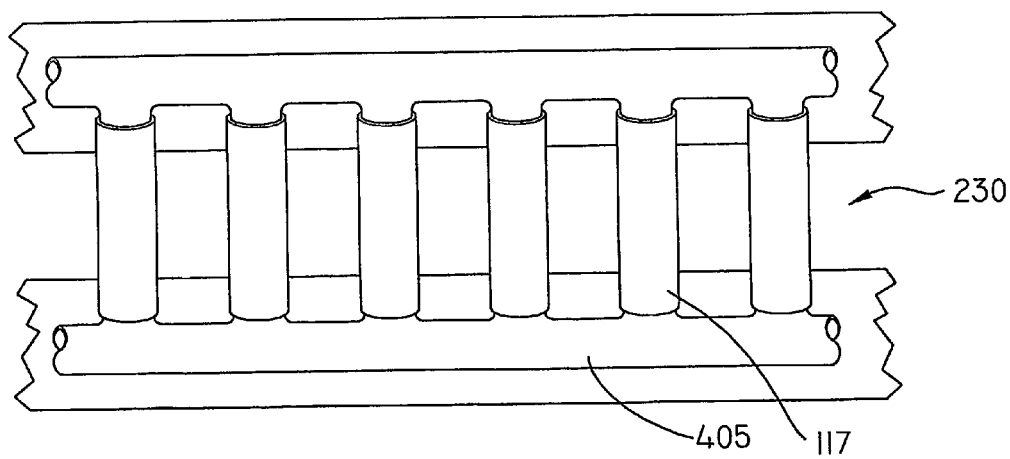
FIG. 13B shows an alternative embodiment of a traction device with molded manifolds.

FIG. 13B shows a variation with molded manifolds 405. Manifolds 405 may be shaped to adapt to the portion of anatomy to be tensioned.

Figure 14:
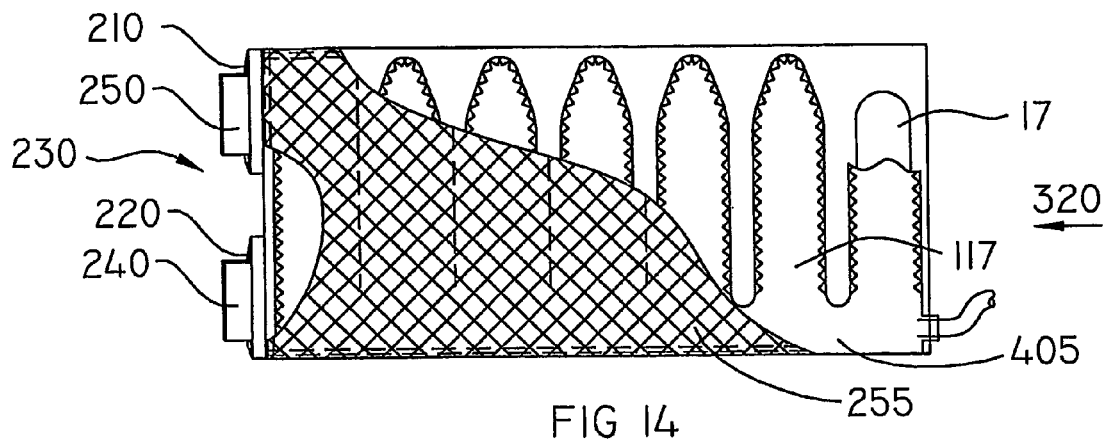
FIG. 14 shows an embodiment of a planar actuator with sewn guides of an asymmetrically elastic material.

FIG. 14 is a partially cut-away view of a tensioner which includes a sewn guide 117 which constrains a bladder 17 constructed in the shape shown in FIG. 5A. Guide 117 may be made of a cloth having suitable asymmetrical elastic properties. Manifold portion 405 of guide 117 is made from relatively inelastic fabric so as to minimize expansion of the actuator in the low-stretch direction indicated by arrow 320. Guide 117 is attached to sleeves 210 and 220 which are arranged around encircling members 250 and 240 respectively to transfer force from actuator 230 to the separation of encircling members 250 and 240. This tensioner may also have a cover 255.

In other contemplated, but unillustrated embodiments of the invention, there may be alternate hip belts and manifolds for tube type traction devices. For example, a manifold may be contained within a hip pad with a row of tube attachments along the upper edge. For lumbar applications it would be preferable to have the attachments close to the bottom to allow longer tubes to be used and enable a greater extension distance range. A lower belt could also have a foam-filled inflatable bladder which may be separately inflatable to provide a well cushioned interface to a wearer's body. A fluid manifold may extend along the edge of the belt with tube attachments emerging at intervals to which tubular actuators may be connected.

In another unillustrated embodiment, a lumbar traction device built with tube type actuators could have manifolds integrated into pads. Additional manifold tubes may be provided to allow a single point of inflation and single pressure for the device. Extending tubes may join the upper encircling member to the lower encircling member and provide the tensioning force.

The number and locations of extending tubes as well as their attachment points to the encircling members and their diameters may vary substantially from that described.

Figure 15A:
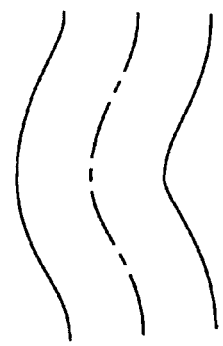
FIGS. 15A and 15B are schematic views of a scoliosis brace which incorporates actuators according to the invention.
Figure 15B:
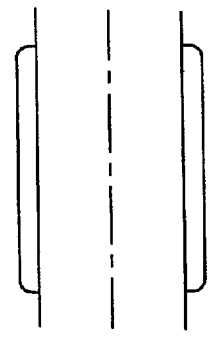

FIGS. 15A and 15B figuratively illustrate a brace which might be useful in the treatment of scoliosis. When inflated the brace applies a load which tends to straighten the wearer's spine. This straightening force could be achieved for example through the use of actuators which bend when they are inflated (for example, as shown in FIG. 5J). Alternately actuators as shown in FIG. 1 in which the two halves of guide 117 exhibit different extension characteristics in the direction shown by arrow 310 may be used. The variability of elastic properties of guide 117 may be obtained by making guide sheets 110 and 120 out of different materials or of different thicknesses of material or by providing different patterns of weakening or stiffening features on guide sheets 110 and 120.

It can be appreciated that the invention may be embodied in devices for applying traction and/or unloading forces to anatomical structures which can have certain desirable characteristics. One such characteristic is that the actuator can be a "soft" component. This enhances comfort in standing, sitting and lying postures as compared to apparatus which includes hard rigid components.

Since the traction force may be generated in a well distributed way the encircling members do not need to be particularly stiff as there is a limited requirement for bridging between actuators. In addition the ergonomic application of force to the human body can be greatly improved with an even distribution of force over a large area resulting in greater comfort for the wearer.

The embodiments of the invention described herein each have various features. Those skilled in the art will understand that the features of any of these embodiments may be combined with features of other disclosed embodiments in to yield other embodiments of the invention.

Where a component (e.g. a member, part, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example, the functions of the bladder and guide may be combined by using a single material which is fluid impermeable and has asymmetrical elastic properties to define the bladder. Accordingly, the scope of the invention is to be construed in accordance with the substance defined by the following claims.

What is claimed is:

1. A device for applying force to a person's spine, the device comprising:
   a first body-encircling member configured to wrap around and grip the person's torso at a first location;
   a second body-encircling member configured to wrap around and grip the person's torso at a second location that is spaced apart from the first location in a first direction along the person's torso; and
   at least one actuator connected between the first and second body-encircling members, the at least one actuator arranged to extend around the person's back and sides, the at least one actuator comprising an inflatable bladder having an asymmetrically elastic wall wherein, upon inflation, the wall constrains the bladder to expand preferentially along an axis extending between the first and second body-encircling members such that when the first and second body-encircling members are wrapped around the person's torso, inflation of the bladder forces the first and second body-encircling members apart, thereby applying traction to the person's spine wherein the device is configured to be free of actuators in its portion extending across a front of the person.

2. A device according to claim 1 wherein the bladder comprises a plurality of transversely-spaced generally-parallel tubular portions in fluid communication through at least one manifold, the tubular portions each expandible lengthwise upon inflation of the bladder and extending between the first and second body-encircling members.

3. A device according to claim 2 wherein the tubular portions extend parallel to the first direction and are closely-spaced to provide a palisade-like arrangement when the bladder is inflated.

4. A device according to claim 3 wherein the wall of the bladder has a higher modulus of elasticity on outward-facing sides of the tubular portions of the actuator than on inward-facing sides of the tubular portions of the actuator.

5. A device according to claim 2 wherein the tubular portions support one another against deflection in a transverse direction when the bladder is inflated.

6. A device according to claim 5 wherein the actuator extends substantially continuously through an angle which is at least 180 degrees and less than 270 degrees as measured relative to a central point on a coronal midline of the person wearing the device.

7. A device according to claim 6 wherein the bladder expands preferentially in a direction lying substantially in a surface defined between the first and second body-encircling members.

8. A device according to claim 2 wherein the wall comprises an air-impermeable layer and a guide.

9. A device according to claim 8 wherein the guide comprises two layers of asymmetrically-elastic material joined at longitudinally-extending seams wherein a high-stretch direction of the material is oriented lengthwise relative to the tubular portions.

10. A device according to claim 9 wherein a low-stretch direction of the material is oriented circumferentially around the tubular portions.

11. A device according to claim 10 wherein the tubular portions are generally cylindrical when the bladder is inflated and wherein portions of the guide that contact the tubular portions are generally cylindrical when the bladder is inflated.

12. A device according to claim 2 wherein, when laid flat, the actuator is generally rectangular and has a width in a direction along the body-encircling members that is greater than a height extending between the body-encircling members.

13. A device according to claim 12 wherein the tubular portions extend substantially at right angles to the body-encircling members.

14. A device according to claim 13 wherein the wall of the actuator in an area on an inner surface of the actuator has a lower modulus of elasticity than that of the wall of the actuator on an area on an outer surface of the actuator.

15. A device according to claim 2 wherein the guide constrains the expansion of the tubular portions asymmetrically, thereby causing the actuator to bend when the bladder is inflated.

16. A device according to claim 1 wherein the at least one actuator extends substantially continuously through an angle which is at least 180 degrees and less than 270 degrees as measured relative to a central point on a coronal midline of the person wearing the device.

17. A device according to claim 16 wherein the device is dimensioned to apply unloading force to a lumbar spine of a person.

18. A device according to claim 1 wherein the asymmetrically elastic wall comprises a woven asymmetrically-elastic material having a high-stretch direction oriented parallel to the first direction.

19. A device according to claim 1 wherein
the at least one actuator comprises one or more actuators arranged along the first and second body encircling members so as to extend substantially continuously through an angle which is more that 180 degrees and less than 270 degrees as measured relative to a central point on a coronal midline of the person wearing the device.

20. A device according to claim 1 wherein the first and second body encircling members are dimensioned to extend around a torso of the person and the at least one actuator is dimensioned to extend substantially continuously around sides and back of the person's torso while leaving a front of the person's torso unobstructed by the at least one actuator.

21. A device according to claim 1 wherein a forwardmost position of the actuator relative to a torso coronal midline of the person is less than about 5 inches.

22. A device for applying force to a person's spine, the device comprising:
a first body-encircling member configured to wrap around and grip the person's torso at a first location;
a second body-encircling member configured to wrap around and grip the person's torso at a second location that is spaced apart from the first location in a first direction along the person's torso; and
a first actuator connected between the first and second body-encircling members and located to be adjacent a first hip of the person wearing the device and a second actuator connected between the first and second body-encircling members and located to be adjacent a second hip of the person wearing the device,
each one of the actuators comprising an inflatable bladder having an asymmetrically elastic wall wherein, upon inflation, the wall constrains the bladder to expand preferentially along an axis extending between the first and second body-encircling members such that when the first and second body-encircling members are wrapped around the person's torso, inflation of the bladder forces the first and second body-encircling members apart, thereby applying traction to the person's spine,
wherein, when the device is worn with the first and second actuators adjacent the person's hips, the first and second actuators do not extend across the person's front.

23. A device according to claim 22 wherein the first and second actuators are individually adjustable.

24. A method for applying force to a person's spine, the method comprising:
providing a device comprising first and second body-encircling members, an inflatable bladder having an asymmetrically-elastic wall connected between the first and second body-encircling members;
securing the first body-encircling member around the person's torso at a first location;
securing the second body-encircling member around the person's torso at a second location spaced apart from the first location in a direction along the person's torso so that the inflatable bladder extends around the person's back and sides while leaving the person's front open; and
inflating the bladder;

whereby, upon inflation, the asymmetrically-expandable wall causes the bladder to expand preferentially in a direction that forces the first and second body-encircling members apart thereby applying traction to the person's spine.

25. A method according to claim 24 wherein the bladder comprises a plurality of transversely spaced generally parallel tubular portions and inflating the bladder comprises allowing the tubular portions to support one another in a closely-spaced palisade-like arrangement.

26. A method according to claim 25 wherein the wall of the bladder has a lower modulus of elasticity on inward-facing sides of the tubular portions of the actuator than on outward-facing sides of the tubular portions of the actuator and the method comprises, allowing the tubular portions to bow inwardly during inflation of the bladder.

27. A method according to claim 24 wherein the portion of the spine to which force is applied is a lumbar spine of the person and securing the first and second body-encircling members comprises:

securing the first body-encircling member around the person's torso below the lumbar spine such that the portion of the first and second body-encircling members that is connected to the bladder extends across a back of the person; and, securing the second body-encircling member around the person's torso above the lumbar spine.

* * * * *